United States Patent
Moran et al.

(10) Patent No.: US 9,802,890 B2
(45) Date of Patent: *Oct. 31, 2017

(54) PROCESSES FOR THE CONVERGENT SYNTHESIS OF CALICHEAMICIN DERIVATIVES

(71) Applicant: WYETH LLC, New York, NY (US)

(72) Inventors: Justin Keith Moran, Valley Cottage, NY (US); Jianxin Gu, River Edge, NJ (US)

(73) Assignee: WYETH LLC, New York, NY (US)

( * ) Notice: Subject to any disclaimer, the term of this patent is extended or adjusted under 35 U.S.C. 154(b) by 75 days.

This patent is subject to a terminal disclaimer.

(21) Appl. No.: 14/711,267

(22) Filed: May 13, 2015

(65) Prior Publication Data

US 2015/0315138 A1 Nov. 5, 2015

Related U.S. Application Data

(60) Division of application No. 14/025,588, filed on Sep. 12, 2013, now abandoned, which is a continuation of application No. 13/624,118, filed on Sep. 21, 2012, now Pat. No. 8,546,549, which is a continuation of application No. 12/583,237, filed on Aug. 17, 2009, now Pat. No. 8,273,862, which is a continuation of application No. 11/708,849, filed on Feb. 20, 2007, now abandoned.

(60) Provisional application No. 60/775,370, filed on Feb. 21, 2006.

(51) Int. Cl.
| | | |
|---|---|---|
| *C07C 323/60* | (2006.01) | |
| *C07D 207/46* | (2006.01) | |
| *C07C 319/20* | (2006.01) | |
| *C07D 207/404* | (2006.01) | |
| *C07D 309/14* | (2006.01) | |
| *C07D 405/14* | (2006.01) | |
| *C07H 15/203* | (2006.01) | |
| *C07H 15/26* | (2006.01) | |

(52) U.S. Cl.
CPC .......... *C07C 323/60* (2013.01); *C07C 319/20* (2013.01); *C07D 207/404* (2013.01); *C07D 207/46* (2013.01); *C07D 309/14* (2013.01); *C07D 405/14* (2013.01); *C07H 15/203* (2013.01); *C07H 15/26* (2013.01)

(58) Field of Classification Search
None
See application file for complete search history.

(56) References Cited

U.S. PATENT DOCUMENTS

| | | |
|---|---|---|
| 4,970,198 A | 11/1990 | Lee et al. |
| 5,053,394 A | 10/1991 | Ellestad et al. |
| 5,108,912 A | 4/1992 | Lee et al. |
| 5,739,116 A | 4/1998 | Hamann et al. |
| 5,770,701 A | 6/1998 | McGahren et al. |
| 5,773,001 A | 6/1998 | Hamann et al. |
| 5,877,296 A | 3/1999 | Hamann et al. |

OTHER PUBLICATIONS

Philip R. Hamann et al., "Gemtuzumab Ozogamicin, A Potent and Selective Anti-CD33 Antibody-Calicheamicin Conjugate for Treatment of Acute Myeloid Leukemia" *Bioconjugate Chemistry*, vol. 13, 2002, pp. 47-58.

Siegel, Marshall, et al, "Calicheamicin Derivatives Conjugated to Monoclonal Antibodies: Determination of Loading Values and Distributions of Infrared and UV Matrix-Assisted Laser Desorption/Ionization Mass Spectrometry and Electrospray Ionization Mass Spectrometry" *Analytical Chemistry* (1997) vol. 69, pp. 2716-2726.

*Primary Examiner* — Layla Berry
(74) *Attorney, Agent, or Firm* — Womble Carlyle Sandridge & Rice, LLP

(57) ABSTRACT

This invention describes processes for the convergent synthesis of calicheamicin derivatives, and similar analogs using bifunctional and trifunctional linker intermediates.

28 Claims, No Drawings

PROCESSES FOR THE CONVERGENT SYNTHESIS OF CALICHEAMICIN DERIVATIVES

FIELD OF THE INVENTION

This is a divisional of U.S. patent application Ser. No. 14/025,588, filed on Sep.12, 2013, which is a continuation of U.S. patent appl. Ser. No. 13/624,118, filed on Sep. 21, 2012 (now U.S. Pat. No. 8,546,549), which claims priority to U.S. patent appl. Ser. No. 12/583,237, filed on Aug. 17, 2009 (now U.S. Pat. No. 8,273,862), which claims priority to U.S. patent appl. Ser. No. 11/708,849, filed on Feb. 20, 2007 (now abandoned), which itself claims priority to U.S. Prov. Patent Appl. No. 60/775,370, filed Feb. 21, 2006, all of which are hereby incorporated herein in entirety.

This invention describes processes for the convergent synthesis of calicheamicin derivatives, and similar analogs using bifunctional and trifunctional linker intermediates.

BACKGROUND OF THE INVENTION

The potent family of antibacterial and antitumor agents known collectively as the calicheamicins or the LL-E33288 complex, are disclosed in U.S. Pat. No. 4,970,198 (1990). The compounds contain a methyltrisulfide that can be reacted with appropriate thiols to form disulfides while at the same time introducing a functional group such as a hydrazide or similar nucleophile. Examples of this reaction with the calicheamicins are given in U.S. Pat. No. 5,053,394. U.S. Pat. No. 5,770,701 is directed to a process for preparing targeted forms of disulfide compounds of the LL-E33288 complex. A linker, 4-(4-acetyl-phenoxy)butanoic acid, is condensed with calicheamicin N-acetyl gamma dimethyl hydrazide to afford the carboxylic acid-hydrazone which is further treated with N-hydroxysuccinimide to give the OSu ester (N-succinimidyloxy) which is ready for conjugation with a chosen biomacromolecule.

Previously disclosed synthetic methods for constructing calicheamicin derivatives are complicated by multiple calicheamicin containing synthetic steps having low overall yields. The calicheamicin moiety is inherently toxic, and when already part of a synthetic target necessitates increased safety precautions which must be observed during manipulation and purification of the products of each of the synthetic steps. The claimed process provides a method of fewer steps involving the calicheamicin moiety with increased yields.

SUMMARY OF THE INVENTION

Discussed herein is a process to prepare calicheamicin derivatives of Formula (I):

Formula (I)

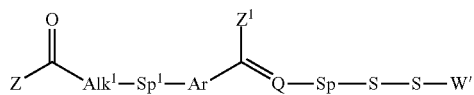

wherein:
Z is selected from the group consisting of

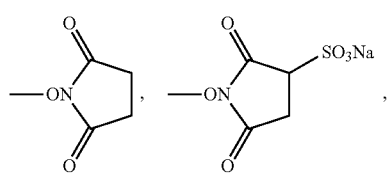

-continued

$Alk^1$ is a branched or unbranched alkylene chain of 2 to 6 carbon atoms;
$Sp^1$ is selected from —S—, —O—, —CONH—, —NHCO—, and —NR'—;
$Z^1$ is H, or alkyl of 1 to 5 carbon atoms;
Ar is 1,2-, 1,3-, or 1,4-phenylene optionally substituted with one, two, or three groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR' or a 1,2-, 1,3-, 1,4-, 1,5-, 1,6-, 1,7-, 1,8-, 2,3-, 2,6-, or 2,7-naphthylidene optionally substituted with one, two, three, or four groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR';
n is an integer from 0 to 5;
R' is a straight or branched alkyl of 1 to 5 carbon atoms optionally substituted by one or two groups of —OH, alkoxy of 1 to 4 carbon atoms, thioalkoxy of 1 to 4 carbon atoms;
Sp is a straight or branched-chain divalent or trivalent alkyl radical of 1 to 18 carbon atoms, divalent or trivalent aryl or heteroaryl radical, divalent or trivalent cycloalkyl of 3 to 18 carbon atoms or heterocycloalkyl radical, divalent or trivalent aryl- or heteroaryl-alkyl (C$_1$-C$_{18}$) radical, divalent or trivalent cycloalkyl- or heterocyclo-alkyl-alkyl (C$_1$-C$_{18}$) radical or divalent or trivalent unsaturated alkyl radical of 2 to 18 carbon atoms, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by dialkylamino of 1 to 5 carbon atoms, alkoxy of 1 to 5 carbon atoms, hydroxy, or alkylthio of 1 to 5 carbon atoms groups;
W' is

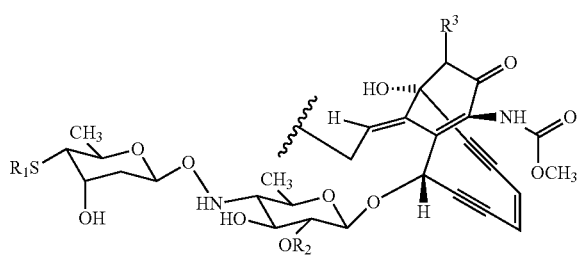

$R_1$ is

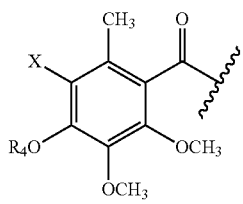

or $CH_3$; $R_2$ is

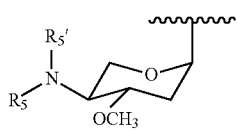

or H;
$R_3$ is

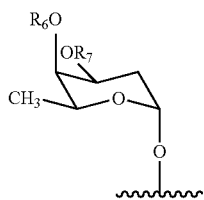

or H; $R_4$ is

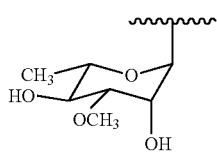 [SMILES: *C1OC(C)C(O)C(OC)C1O]

or H;
$R_6$ or $R_7$ is H or

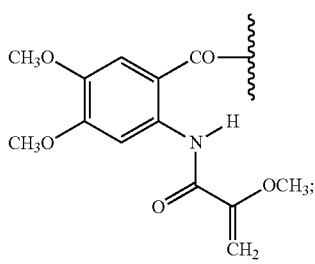

$R_5$ is —$CH_3$, —$C_2H_5$, or —$CH(CH_3)_2$;
X is an iodine or bromine atom;
$R_5'$ is a hydrogen or the group RCO, wherein R is hydrogen, branched or unbranched alkyl of 1 to 10 carbon atoms, alkylene of 2 to 10 carbon atoms, aryl of 6 to 11 carbon atoms, a ($C_6$-$C_{11}$) aryl-alkyl ($C_1$-$C_5$) group, or a heteroaryl or heteroaryl-alkyl ($C_1$-$C_5$) group wherein heteroaryl is defined as 2- or 3-furyl, 2- or 3-thienyl, 2- or 3-(N-methylpyrrolyl), 2-, 3-, or 4-pyridinyl, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl groups optionally substituted by one or more hydroxy, amino, carboxy, halo, nitro, ($C_1$-$C_3$) alkoxy of 1 to 3 carbon atoms, or thioalkoxy of 1 to 5 carbon atoms; and
Q is selected from the group consisting of —NNHCO—, —NNHCS—, —NNHCONH—, —NNHCSNH—, and —NO—;
comprising the steps of:
a. reacting a carboxylic acid of the formula

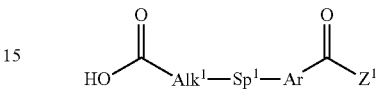

with a mercapto compound of the formula $H_2Q$-Sp-SH in an alcohol solvent in the presence of an alkyl carboxylic acid, $alk^2CO_2H$ where $alk^2$ is 1 to 4 carbon atoms at about 20° to 70° C. for about 1 to 24 hours, wherein $Alk^1$, $Sp^1$, Ar, $Z^1$, Q, and Sp are as defined above, to produce a bilinker-carboxylic acid of the formula, wherein the mercapto compound and carboxylic acid are present in a ratio of about 1.2:1

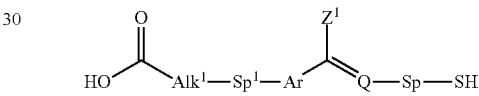

b. isolating the bilinker-carboxylic acid of step (a);
c. reacting the isolated bilinker-carboxylic acid of step (b) with an at least a 3 fold molar excess of N-hydroxysuccinimide, 2,3,5,6-tetrafluorophenol, pentafluorophenol, 4-nitrophenol, 2,4-dinitrophenol, or N-hydroxysulfosuccinimide in the presence of 1,3-dicyclohexylcarbodiimide (DCC), 1-(3-dimethylaminopropyl)-3-ethylcarbodiimide (EDCI), or N,N'-disuccinimdyl carbonate in an inert solvent containing 0-50% N,N-dimethylformamide (DMF) to generate a trilinker-activated ester of the formula

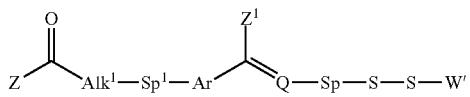

where Z is hereinbefore defined;
d. reacting the trilinker-activated ester formed in step with a methyltrithio antitumor antibiotic $CH_3$—S—S—S—W' in the presence of a base or an organic base with a methyltrithio antitumor antibiotic $CH_3$—S—S—S—W' in an inert organic solvent to generate an activated ester of the formula below, wherein the trilinker-activated ester in step c and the $CH_3$—S—S—S—W' are in a ratio of 3.3:1 and the temperature of the reaction is 5° C.

e. isolating the activated ester of step (d) and purifying to yield antitumor antibiotics of Formula (I)

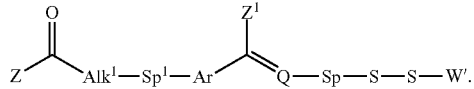
Formula (I)

An additional process discussed includes a method of preparing antitumor antibiotics of Formula (I):

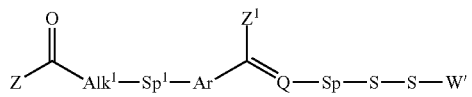
Formula (I)

wherein:
Z is selected from the group consisting of

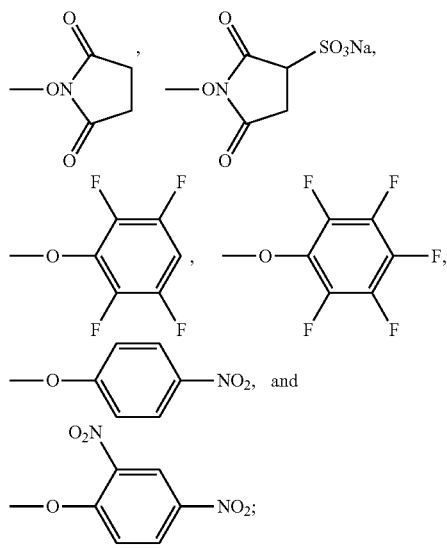

Alk$^1$ is a branched or unbranched alkylene chain of 2 to 6 carbon atoms;
Sp$^1$ is selected from —S—, —O—, —CONH—, —NHCO—, and —NR'—;
Z$^1$ is H, or alkyl of 1 to 5 carbon atoms;
Ar is 1,2-, 1,3-, or 1,4-phenylene optionally substituted with one, two, or three groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR' or a 1,2-, 1,3-, 1,4-, 1,5-, 1,6-, 1,7-, 1,8-, 2,3-, 2,6-, or 2,7-naphthylidene optionally substituted with one, two, three, or four groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR';
n is an integer from 0 to 5;
R' is a straight or branched alkyl of 1 to 5 carbon atoms optionally substituted by one or two groups of —OH, alkoxy of 1 to 4 carbon atoms, thioalkoxy of 1 to 4 carbon atoms;
Sp is a straight or branched-chain divalent or trivalent alkyl radical of 1 to 18 carbon atoms, divalent or trivalent aryl or heteroaryl radical, divalent or trivalent cycloalkyl of 3 to 18 carbon atoms or heterocycloalkyl radical, divalent or trivalent aryl- or heteroaryl-alkyl (C$_1$-C$_{18}$) radical, divalent or trivalent cycloalkyl- or heterocyclo-alkyl-alkyl (C$_1$-C$_{18}$) radical or divalent or trivalent unsaturated alkyl radical of 2 to 18 carbon atoms, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by dialkylamino of 1 to 5 carbon atoms, alkoxy of 1 to 5 carbon atoms, hydroxy, or alkylthio of 1 to 5 carbon atoms groups;
W' is

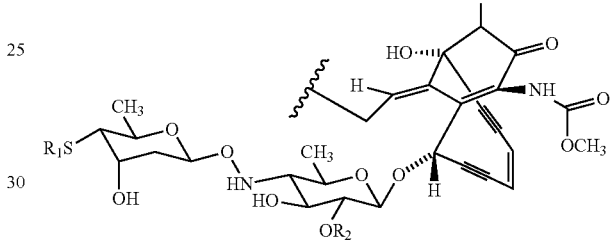

R$_1$ is

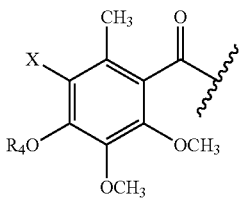

or CH$_3$; R$_2$ is

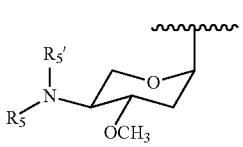

or H;
R$_3$ is

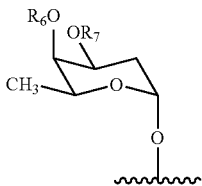

or H; R$_4$ is

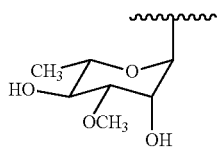

or H;
R$_6$ or R$_7$ is H or

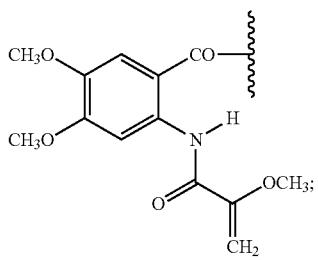

R$_5$ is —CH$_3$, —C$_2$H$_5$, or —CH(CH$_3$)$_2$;
X is an iodine or bromine atom;
R$_5$' is a hydrogen or the group RCO, wherein R is hydrogen, branched or unbranched alkyl of 1 to 10 carbon atoms, alkylene of 2 to 10 carbon atoms, aryl of 6 to 11 carbon atoms, a (C$_6$-C$_{11}$) aryl-alkyl (C$_1$-C$_5$) group, or a heteroaryl or heteroaryl-alkyl (C$_1$-C$_5$) group wherein heteroaryl is defined as 2- or 3-furyl, 2- or 3-thienyl, 2- or 3-(N-methylpyrrolyl), 2-, 3-, or 4-pyridinyl, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl groups optionally substituted by one or more hydroxy, amino, carboxy, halo, nitro, (C$_1$-C$_3$) alkoxy of 1 to 3 carbon atoms, or thioalkoxy of 1 to 5 carbon atoms; and
Q is selected from the group consisting of —NNHCO—, —NNHCS—, —NNHCONH—, —NNHCSNH—, and —NO—;
comprising the steps of:
a. reacting a carboxylic acid of the formula

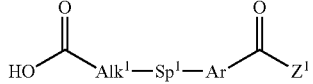

with a mercapto compound of the formula

in an alcohol solvent in the presence of an alkyl carboxylic acid, alk$^2$CO$_2$H where alk$^2$ is 1 to 4 carbon atoms at about 20° to 70° C. for about 1 to 24 hours, wherein Alk$^1$, Sp$^1$, Ar, Z$^1$, Q, and Sp are as defined above, to produce a bilinker-carboxylic acid of the formula, wherein the mercapto compound and carboxylic acid are present in a ratio of about 1.2:1

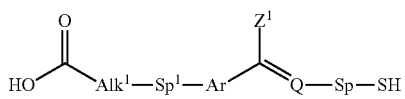

b. isolating the bilinker-carboxylic acid of step (a);
c. reacting the isolated bilinker-carboxylic acid of step (b) with CH$_3$—S—S—S—W' in the presence of a base or an organic base with a methyltrithio antitumor antibiotic CH$_3$—S—S—S—W' in an inert organic solvent;
d. reacting the compound of step (c) with an at least a 3 fold molar excess of N-hydroxysuccinimide, 2,3,5,6-tetrafluorophenol, pentafluorophenol, 4-nitrophenol, 2,4-dinitrophenol, or N-hydroxysulfosuccinimide in the presence of 1,3-dicyclohexylcarbodiimide (DCC), 1-(3-dimethylaminopropyl)-3-ethylcarbodiimide (EDCI), or N,N'-disuccinimdyl carbonate in an inert solvent containing 0-50% N,N-dimethylformamide (DMF) and purifying to yield compounds of Formula (I)

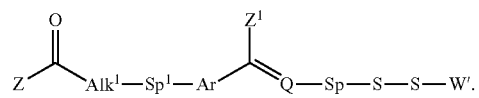

An additional process includes preparation of compounds of Formula (I):

Formula (I)

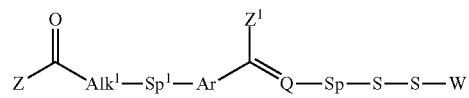

wherein:
Z is selected from the group consisting of

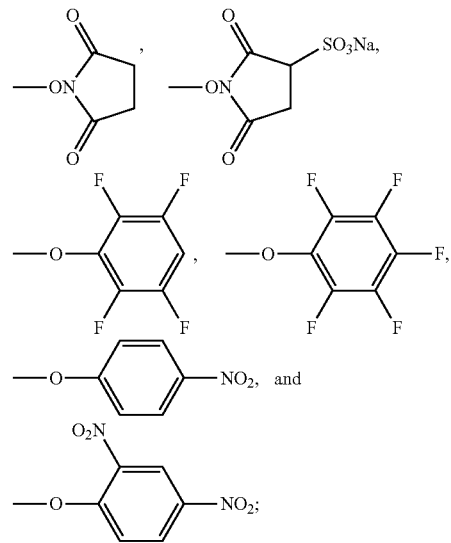

Alk$^1$ is a branched or unbranched alkylene chain of 2 to 6 carbon atoms;
Sp$^1$ is selected from —S—, —O—, —CONH—, —NHCO—, and —NR'—;
Z$^1$ is H, or alkyl of 1 to 5 carbon atoms;
Ar is 1,2-, 1,3-, or 1,4-phenylene optionally substituted with one, two, or three groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR' or a 1,2-, 1,3-, 1,4-, 1,5-, 1,6-, 1,7-, 1,8-, 2,3-, 2,6-, or 2,7-naphthylidene optionally substituted with one, two, three, or four groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR';

n is an integer from 0 to 5;

R' is a straight or branched alkyl of 1 to 5 carbon atoms optionally substituted by one or two groups of —OH, alkoxy of 1 to 4 carbon atoms, thioalkoxy of 1 to 4 carbon atoms;

Sp is a straight or branched-chain divalent or trivalent alkyl radical of 1 to 18 carbon atoms, divalent or trivalent aryl or heteroaryl radical, divalent or trivalent cycloalkyl of 3 to 18 carbon atoms or heterocycloalkyl radical, divalent or trivalent aryl- or heteroaryl-alkyl (C$_1$-C$_{18}$) radical, divalent or trivalent cycloalkyl- or heterocyclo-alkyl-alkyl (C$_1$-C$_{18}$) radical or divalent or trivalent unsaturated alkyl radical of 2 to 18 carbon atoms, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by dialkylamino of 1 to 5 carbon atoms, alkoxy of 1 to 5 carbon atoms, hydroxy, or alkylthio of 1 to 5 carbon atoms groups;

W' is

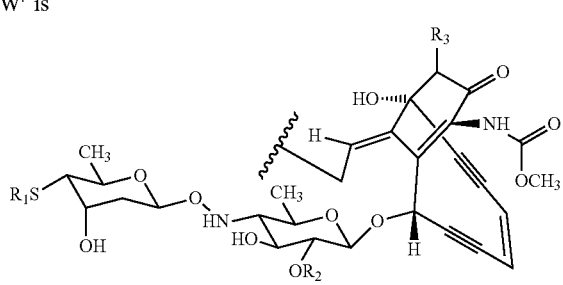

R$_1$ is

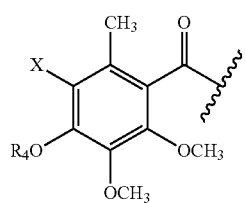

or CH$_3$; R$_2$ is

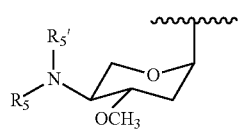

or H;

R$_3$ is

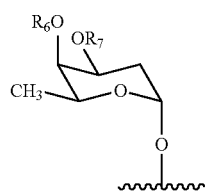

or H; R$_4$ is

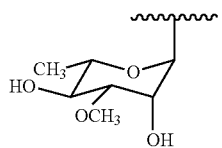 [SMILES: *C1OC(C)C(O)C(OC)C1O]

or H;

R$_6$ or R$_7$ is H or

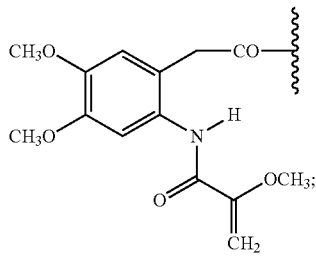

R$_5$ is —CH$_3$, —C$_2$H$_5$, or —CH(CH$_3$)$_2$;

X is an iodine or bromine atom;

R$_5$' is a hydrogen or the group RCO, wherein R is hydrogen, branched or unbranched alkyl of 1 to 10 carbon atoms, alkylene of 2 to 10 carbon atoms, aryl of 6 to 11 carbon atoms, a (C$_6$-C$_{11}$) aryl-alkyl (C$_1$-C$_5$) group, or a heteroaryl or heteroaryl-alkyl (C$_1$-C$_5$) group wherein heteroaryl is defined as 2- or 3-furyl, 2- or 3-thienyl, 2- or 3-(N-methylpyrrolyl), 2-, 3-, or 4-pyridinyl, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl groups optionally substituted by one or more hydroxy, amino, carboxy, halo, nitro, (C$_1$-C$_3$) alkoxy of 1 to 3 carbon atoms, or thioalkoxy of 1 to 5 carbon atoms; and Q is selected from the group consisting of —NNHCO—, —NNHCS—, —NNHCONH—, —NNHCSNH—, and —NO—;

comprising the steps of:

a. reacting a carboxylic acid of the formula

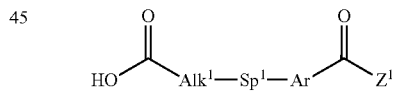

with a mercapto compound of the formula

H$_2$Q-Sp-SH in an alcohol solvent in the presence of an alkyl carboxylic acid, alk$^2$CO$_2$H where alk$^2$ is 1 to 4 carbon atoms at about 20° to 70° C. for about 1 to 24 hours, wherein Alk$^1$, Sp$^1$, Ar, Z$^1$, Q, and Sp are as defined above, to produce a bilinker-carboxylic acid of the formula,

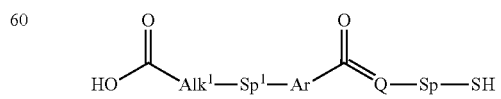

b. isolating the bilinker-carboxylic acid of step (a);

c. reacting the isolated bilinker-carboxylic acid of step (b) with an at least of N-hydroxysuccinimide, 2,3,5,6-tetrafluorophenol, pentafluorophenol, 4-nitrophenol, 2,4-dinitrophenol, or N-hydroxysulfosuccinimide in the presence of 1,3-dicyclohexylcarbodiimide (DCC), 1-(3-dimethylaminopropyl)-3-ethylcarbodiimide (EDCI), or N,N'-disuccinimdyl carbonate in an inert solvent containing 0-50% N,N-dimethylformamide (DMF) to generate a trilinker-activated ester of the formula

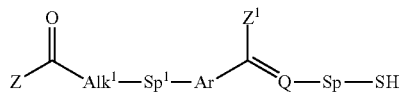

where Z is hereinbefore defined;

d. reacting the trilinker-activated ester in step c in the presence of a base or an organic base with $CH_3$—S—W' in an inert organic solvent to generate an activated ester of the formula

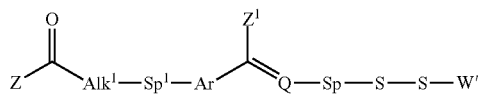

e. isolating the activated ester of step (d) and purifying to yield compounds of Formula (I)

Formula (I)

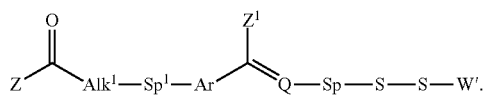

The processes include a purifying of step comprising the use of a reverse phase high performance liquid chromatography having a mobile phase of about pH 7.0 to 9.0 followed with a normal phase chromatography.

The processes include:
$alk^1$ is 3 carbon atoms;
$Sp^1$ is —O—;
$Z^1$ is methyl;
Ar is unsubstituted 1,4-phenylene;
Sp is 4 carbon atoms;
$R_3$ is H;
Q is NNHC(O)—;
$R_2$ is

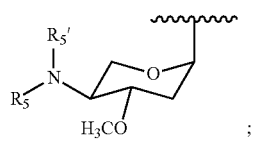

$R_4$ is

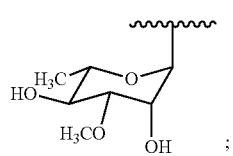 [SMILES: *C1OC(C)C(O)C(OC)C1O]

$R_5$ is $C_2H_5$;
$R_5'$ is —C(O)—R;
R is methyl; and
Z is

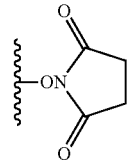

The processes include but are not limited to $Alk^1$ is an alkylene of 2 to 5 carbon atoms, and $Sp^1$ is an oxygen atom.

The processes include but are not limited $Alk^1$ is an alkylene of 3 carbon atoms.

The processes include but are not limited $Z^1$ is alkyl of 1 to 3 carbon atoms.

The processes include but are not limited Ar is 1,2-, 1,3-, or 1,4-phenylene, or 1,2-, 1,3-, 1,4-, 1,5-, 1,6-, 1,7-, 1,8-, 2,3-, 2,6-, or 2,7-naphthylidene.

The processes include but are not limited Ar is 1,4-phenylene.

The processes include but are not limited Q is —NNHCO—.

The processes include but are not limited Sp is straight or branched-chain divalent or trivalent alkyl radical of 1 to 12 carbon atoms.

The processes include but are not limited Sp is straight or branched-chain divalent or trivalent alkyl radical of 1 to 6 carbon atoms.

The processes include but are not limited the alcohol solvent is methanol.

The processes include but are not limited the inert solvent is acetonitrile.

The processes include but are not limited alkyl carboxylic acid is acetic acid.

The processes include but are not limited the inert organic solvent is acetonitrile.

The processes include but are not limited Z is

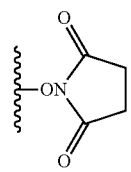

Discussed herein is a process to prepare trilinker-activated esters of the formula:

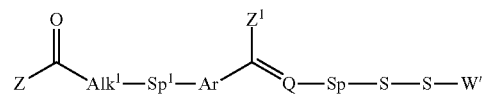

wherein:
Z is selected from the group consisting of

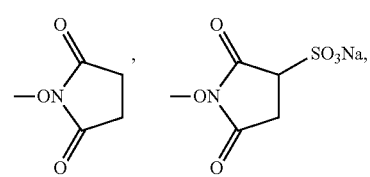

-continued

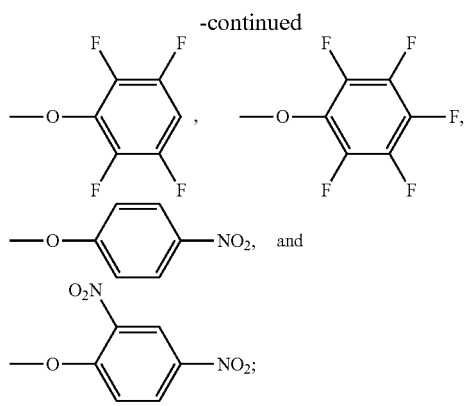

Alk¹ is a branched or unbranched alkylene chain of 2 to 6 carbon atoms;
Sp¹ is selected from —S—, —O—, —CONH—, —NHCO—, and —NR'—;
Z¹ is H, or alkyl of 1 to 5 carbon atoms;
Ar is 1,2-, 1,3-, or 1,4-phenylene optionally substituted with one, two, or three groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR' or a 1,2-, 1,3-, 1,4-, 1,5-, 1,6-, 1,7-, 1,8-, 2,3-, 2,6-, or 2,7-naphthylidene optionally substituted with one, two, three, or four groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR';
n is an integer from 0 to 5;
R' is a straight or branched alkyl of 1 to 5 carbon atoms optionally substituted by one or two groups of —OH, alkoxy of 1 to 4 carbon atoms, thioalkoxy of 1 to 4 carbon atoms;
Sp is a straight or branched-chain divalent or trivalent alkyl radical of 1 to 18 carbon atoms, divalent or trivalent aryl or heteroaryl radical, divalent or trivalent cycloalkyl of 3 to 18 carbon atoms or heterocycloalkyl radical, divalent or trivalent aryl- or heteroaryl-alkyl (C$_1$-C$_{18}$) radical, divalent or trivalent cycloalkyl- or heterocyclo-alkyl-alkyl (C$_1$-C$_{18}$) radical or divalent or trivalent unsaturated alkyl radical of 2 to 18 carbon atoms, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by dialkylamino of 1 to 5 carbon atoms, alkoxy of 1 to 5 carbon atoms, hydroxy, or alkylthio of 1 to 5 carbon atoms groups;
W' is

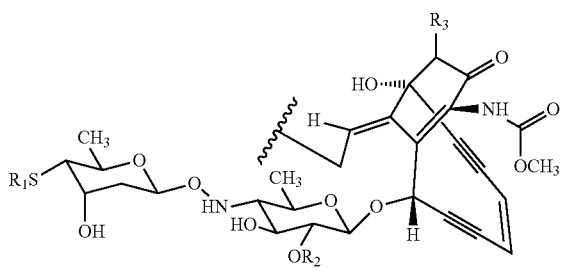

R$_1$ is

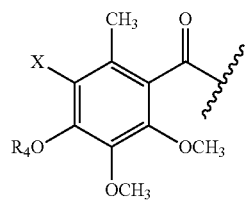

or CH$_3$; R$_2$ is

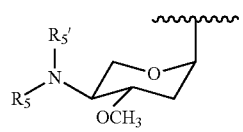

or H;
R$_3$ is

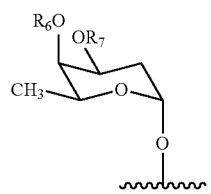

or H; R$_4$ is

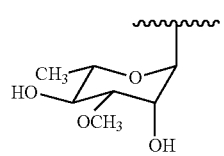 [SMILES: *C1OC(C)C(O)C(OC)C1O]

or H;
R$_6$ or R$_7$ is H or

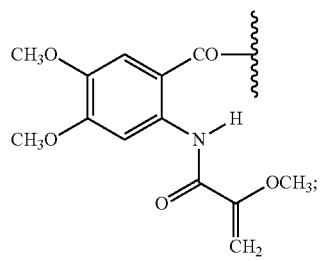

R$_5$ is —CH$_3$, —C$_2$H$_5$, or —CH(CH$_3$)$_2$;
X is an iodine or bromine atom;
R$_5$' is a hydrogen or the group RCO, wherein R is hydrogen, branched or unbranched alkyl of 1 to 10 carbon atoms, alkylene of 2 to 10 carbon atoms, aryl of 6 to 11 carbon atoms, a (C$_6$-C$_{11}$) aryl-alkyl (C$_1$-05) group, or a heteroaryl or heteroaryl-alkyl (C$_1$-05) group wherein heteroaryl is defined as 2- or 3-furyl, 2- or 3-thienyl, 2- or 3-(N-methylpyrrolyl), 2-, 3-, or 4-pyridinyl, 2-, 4-, or 5-(N- methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl groups optionally substituted by one or more hydroxy, amino, carboxy, halo, nitro, ($C_1$-$C_3$) alkoxy of 1 to 3 carbon atoms, or thioalkoxy of 1 to 5 carbon atoms; and Q is selected from the group consisting of —NNHCO—, —NNHCS—, —NHNCONH—, —NNCSNH—, and —NO—;

comprising the steps of:

a. reacting a carboxylic acid of the formula

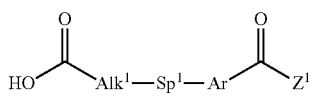

with a mercapto compound of the formula

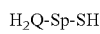

in an alcohol solvent in the presence of an alkyl carboxylic acid, $alk^2CO_2H$ where $alk^2$ is 1 to 4 carbon atoms at about 20° to 70° C. for about 1 to 24 hours, wherein $Alk^1$, $Sp^1$, Ar, $Z^1$, Q, and Sp are as defined above, to produce a bilinker-carboxylic acid of the formula

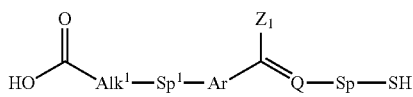

b. isolating the bilinker-carboxylic acid of step (a);

c. reacting the bilinker-carboxylic acid from step (b) in the presence of a base or an organic base with $CH_3$—S—W' in an inert organic solvent to generate a bilinker-methyltrithio compound of the formula

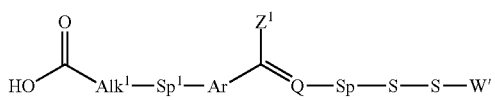

d. reacting the isolated bilinker-methyltrithio compound of step (c) with N-hydroxysuccinimide, 2,3,5,6-tetrafluorophenol, pentafluorophenol, 4-nitrophenol, 2,4-dinitrophenol, or N-hydroxysulfosuccinimide in the presence of 1,3-dicyclohexylcarbodiimide (DCC), 1-(3-dimethylaminopropyl)-3-ethylcarbodiimide (EDCI), or N,N'-disuccinimdyl carbonate in an inert solvent containing 0-50% N,N-dimethylformamide (DMF) to generate a trilinker-activated ester of the formula

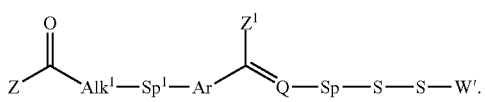

Presented herein is a process for the preparation of trifunctional linker intermediates, of the formula

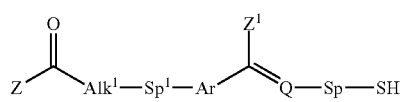

wherein:

$Alk^1$ is a branched or unbranched alkylene chain of 2 to 6 carbon atoms;

$Sp^1$ is selected from —S—, —O—, —CONH—, —NHCO—, and —NR'—;

$Z^1$ is H, or alkyl of 1 to 5 carbon atoms;

Ar is 1,2-, 1,3-, or 1,4-phenylene optionally substituted with one, two, or three groups independently selected from alkyl of 1 to 6 carbon atoms, alkoxy of 1 to 5 carbon atoms, thioalkoxy of 1 to 4 carbon atoms, halogen, nitro, —COOR', —CONHR', —O($CH_2$)$_n$COOR', —S($CH_2$)$_n$COOR', —O($CH_2$)$_n$CONHR', and —S($CH_2$)$_n$CONHR' or a 1,2-, 1,3-, 1,4-, 1,5-, 1,6-, 1,7-, 1,8-, 2,3-, 2,6-, or 2,7-naphthylidene optionally substituted with one, two, three, or four groups independently selected from alkyl of 1 to 6 carbon atoms, alkoxy of 1 to 5 carbon atoms, thioalkoxy of 1 to 4 carbon atoms, halogen, nitro, —COOR', —CONHR', —O($CH_2$)$_n$COOR', —S($CH_2$)$_n$COOR', —O($CH_2$)$_n$CONHR', and —S($CH_2$)$_n$CONHR';

n is an integer from 0 to 5;

R' is a straight or branched alkyl of 1 to 5 carbon atoms optionally substituted by one or two groups of —OH, alkoxy of 1 to 4 carbon atoms, thioalkoxy of 1 to 4 carbon atoms;

Sp is a straight or branched-chain divalent or trivalent alkyl radical of 1 to 18 carbon atoms, divalent or trivalent aryl or heteroaryl radical, divalent or trivalent cycloalkyl of 3 to 18 carbon atoms or heterocycloalkyl radical, divalent or trivalent aryl- or heteroaryl-alkyl ($C_1$-$C_{18}$) radical, divalent or trivalent cycloalkyl- or heterocyclo-alkyl-alkyl ($C_1$-$C_{18}$) radical or divalent or trivalent unsaturated alkyl radical of 2 to 18 carbon atoms, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by dialkylamino of 1 to 5 carbon atoms, alkoxy of 1 to 5 carbon atoms, hydroxy, or alkylthio of 1 to 5 carbon atoms groups;

Q is selected from the group consisting of —NNHCO—, —NNHCS—, and —NNHCONH—;

Z is selected from the group consisting of

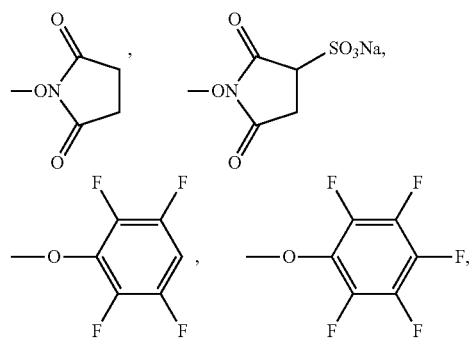

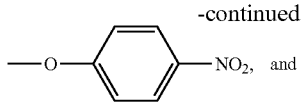

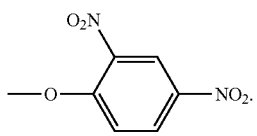

comprising the steps of:
a. reacting a carboxylic acid of the formula

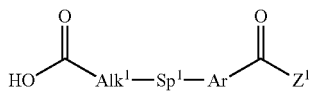

with a mercapto compound of the formula

in an alcohol solvent in the presence of an alkyl carboxylic acid, alk$^2$CO$_2$H, where alk$^2$ is 1 to 4 carbon atoms at about 20° to 70° C. for about 1 to 24 hours, wherein Alk$^1$, Sp$^1$, Ar, Z$^1$, Q, and Sp are as defined above, to produce a bilinker-carboxylic acid of the formula

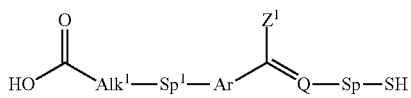

b. isolating the bilinker-carboxylic acid of step (a);
c. reacting the isolated bilinker-carboxylic acid of step (b) with
N-hydroxysuccinimide, 2,3,5,6-tetrafluorophenol, pentafluorophenol, 4-nitrophenol, 2,4-dinitrophenol, or N-hydroxysulfosuccinimide in the presence of 1,3-dicyclohexylcarbodiimide (DCC), 1-(3-dimethylaminopropyl)-3-ethylcarbodiimide (EDCI), or N,N'-disuccinimdyl carbonate in an inert solvent containing 0-50% DMF to generate trifunctional linker intermediates, of the formula

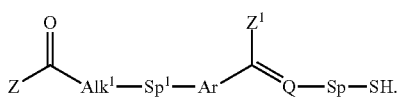

The terms used in this specification generally have their ordinary meanings in the art, within the context of the invention, and in the specific context where each term is used. Certain terms are discussed below, or elsewhere in the specification, to provide additional guidance to the practitioner in describing the compounds, compositions, and methods of the invention and how to make and use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. The use of examples anywhere in this specification, including examples of any terms discussed herein, is illustrative only, and in no way limits the scope and meaning of the invention or of any exemplified term. Likewise, the invention is not limited to the examples presented.

The terms, "about" or "approximately" shall generally mean within 20 percent, preferably within 10 percent, and more preferably within 5 percent of a given value or range.

The term "alkoxy" as used herein refers to an alkyl group, as defined above, having an oxygen radical attached thereto. The term "thioalkoxy" refers to an alkoxy group as defined, having a sulfur radical attached thereto.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In an embodiment, a straight chain or branched chain alkyl has 6 or fewer carbon atoms in its backbone.

The term "alkyl" can be used alone or as part of a chemical name.

The term "aryl" is defined as an aromatic carbocyclic moiety and may be substituted or unsubstituted. Aryl groups have 6 to 14 carbon atoms and include phenyl and napthyl. The term "aryl" also includes polycyclic ring systems having two or more rings in which two or more carbons are common to two adjoining rings (the rings are "fused") wherein at least one of the carbocyclic rings is aromatic, e.g., the other rings can be cycloalkyls, cycloalkenyls, cycloalkynyls, and/or aryls.

Carboxy is defined as a —CO$_2$H radical.

The term "halogen" or "halo" refers to an atom of fluorine, chlorine, bromine, or iodine.

The term "heteroaryl" refers to a 4 to 10 membered ring structure, which ring structure includes one to four heteroatoms. A heteroaryl comprises a heterocyclic ring system of one to three fused rings, in which at least one ring may have an aromatic character and contains 1 to 4 heteroatoms the same or different selected from the group consisting of S, N, and O. The remaining rings of the ring system may be fully unsaturated, partially saturated, or fully saturated. Each ring comprises three to ten members. The term "heteroatom" as used herein means an atom of any element other than carbon or hydrogen and include for example nitrogen, oxygen, sulfur, phosphorus, and selenium.

The term "nitro" means —NO$_2$.

The term "substituted" is contemplated to include all permissible substituents of organic compounds. In a broad aspect, the permissible substituents of organic compounds include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The term alkyl means a straight or branched alkyl of 1 to 18 carbon atoms, preferably 2 to 5 carbon atoms, 1 to 4 carbon atoms or 1 to 3 carbon atoms. In some embodiments of the invention the term alkyl is methyl.

The term alcohol solvent means methanol, ethanol and the like with a boiling point of less than about 100° C.

Alkylene refers to an alkyl, as defined above, which is a diradical, rather than a radical. An alkylene can be branched or unbranched and can have 2-18 carbons.

Ambient temperature is about 25° C.

Inert solvent or inert organic solvent describes a solvent that will neither react or form a covalent bond in the steps to prepare compounds of Formula (I), trilinker-activated esters or trifunctional linker intermediates as described herein. An example of an inert solvent or inert organic solvent may be mixtures such as but not limited to acetonitrile/ethylacetate (1:1)), dichloromethane, N,N-dimethylformamide, tetrahydrofuran, dioxane or acetonitrile. An inert solvent may contain 0-50% N,N-dimethylformamide. An inert organic solvent is for example acetonitrile, ethyl acetate or dichloromethane.

An organic base is for example an alkylamine base which includes triethylamine, N,N-diethylmethylamine, N,N-diethylaniline, N,N-diethylethylenediamine, N,N-diisopropylethylamine, tributylamine or tripropylamine and further include dimethylaminopyridine (DMAP) with diisopropylethylamine (DIEA), N-methylmorpholine, N-methylpyrrolidine, 2,6-di-tertbutyl-4-methylpyridine or pyridine. A base is an alkali metal hydroxide, alkali metal carbonate or alkali metal bicarbonate.

DETAILED DESCRIPTION OF THE INVENTION

The process for the preparation of calicheamicin derivatives of Formula I and tri and bifunctional linker intermediates useful in the preparation of said derivatives of the present invention are described in the following reaction Schemes I and II.

SCHEME I

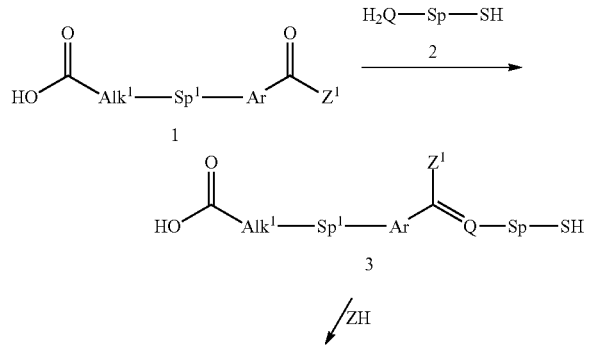

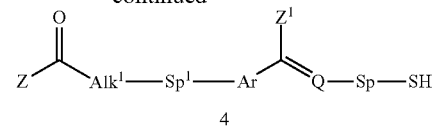

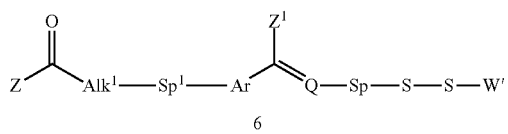

In accordance with Scheme I, a carboxylic acid 1 wherein $Alk^1$, $Sp^1$, Ar and $Z^1$ are hereinbefore defined, found in U.S. Pat. No. 5,773,001, which is hereby incorporated herein by reference, are condensed with mercapto compound 2 where Sp and Q are hereinbefore defined in an alcoholic solvent with a boiling point of less than about 100° C. in the presence of an alkyl carboxylic acid in a about 5% acetic acid at about 20° to about 70° C. for about 1 to about 24 hours, to afford bilinker-carboxylic acid 3 wherein $Alk^1$, $Sp^1$, Ar, Q, Sp and $Z^1$ are as defined above.

Bilinker-carboxylic acid 3 is reacted with N-hydroxysuccinimide, 2,3,5,6-tetrafluorophenol, pentafluorophenol, 4-nitrophenol, 2,4-dinitrophenol, or N-hydroxysulfosuccinimide in the presence of 1,3-dicyclohexylcarbodiimide (DCC), 1-(3-dimethylaminopropyl)-3-ethylcarbodiimide (EDCI), or other carbodiimide or N,N'-disuccinimdyl carbonate in an inert solvent such as dichloromethane, tetrahydrofuran, dioxane, or acetonitrile containing 0-50% DMF or DMF to generate trilinker-activated ester 4 where Z is selected from the group consisting of

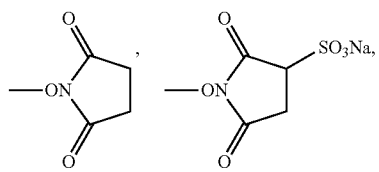

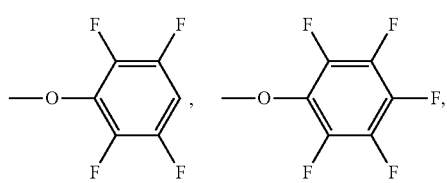

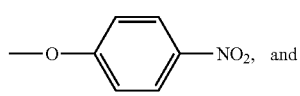, and

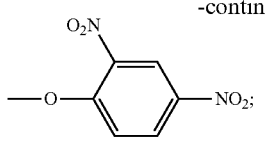

For example, reaction of bilinker-carboxylic acid 3 with a coupling agent, such as 1,3-dicyclohexylcarbodiimide (DCC) or 1-(3-dimethylaminopropyl)-3-ethylcarbodiimide hydrochloride, and N-hydroxysuccinimide or other comparable carboxyl-activating group in an inert solvent, such as N,N-dimethylformamide (DMF), tetrahydrofuran, dioxane or acetonitrile, leads to the formation of a trilinker-activated ester 4, such as the N-hydroxysuccinimide ester described herein. Preferred is N-hydroxysuccinimide, DCC at ambient temperature in dioxane. A preferred solvent mixture is acetonitrile containing 0-50% DMF. Reaction of the bilinker-carboxylic acid 3 with N-hydroxysuccinimide, 2,3,5,6-tetrafluorophenol, pentafluorophenol, 4-nitrophenol, 2,4-dinitrophenol, or N-hydroxysulfosuccinimide in the presence of 1,3-dicyclohexylcarbodiimide (DCC), 1-(3-dimethylaminopropyl)-3-ethylcarbodiimide (EDCI), or other carbodiimide in an inert solvent such as dioxane or acetonitrile containing 0-50% N,N-dimethylformamide (DMF) leads to the formation of a trilinker-activated ester 4. The trilinker-activated ester 4 can be isolated by removal of the volatile solvents and further purified by reverse or normal phase chromatography on an inert support which includes silica-60.

Trilinker-activated ester 4 is first reacted with an alkali metal carbonate which includes but is not limited to sodium carbonate and forms the sodium salt of trilinker-activated ester 4 in acetonitrile by heating at gentle reflux. Further reaction of the sodium salt of trilinker-activated ester 4 with methyltrithioantitumor antibiotic 5 at about −15° C. in an inert organic solvent, preferably acetonitrile gives activated ester 6 wherein Z, Alk$^1$, Sp$^1$, Ar, Z$^1$, Q, Sp and W' are hereinbefore defined. In particular, N-acetyl-LL-E33288 γ$_1^I$ is the preferred methyltrithioantitumor antibiotic 5. Preferred is the reaction in acetonitrile at about 0° C. Optionally an organic base may replace the alkali metal carbonate which preferably includes triethylamine, in acetonitrile at about 0° C.

As further described in Scheme II, reaction of bilinker-carboxylic 3 prepared by condensation of carboxylic acid 1 wherein Alk$^1$, Sp$^1$, Ar and Z$^1$ are hereinbefore defined, with mercapto compound 2 according to scheme I, is reacted with methyltrithioantitumor antibiotic 5 in the presence of triethylamine in N,N-dimethylformamide (DMF) at about −5° C. affords intermediate 7 which is further converted to trilinker-activated ester 6 by reaction with N-hydroxysuccinimide, 2,3,5,6-tetrafluorophenol, pentafluorophenol, 4-nitrophenol, 2,4-dinitrophenol, or N-hydroxysulfosuccinimide in the presence of 1,3-dicyclohexylcarbodiimide (DCC), 1-(3-dimethylaminopropyl)-3-ethylcarbodiimide (EDCI), or other carbodiimide or N,N'-disuccinimdyl carbonate in an inert solvent mixture of DMF and acetonitrile which is then purified preferably by chromatography to afford antitumor antibiotics of Formula (I).

SCHEME II

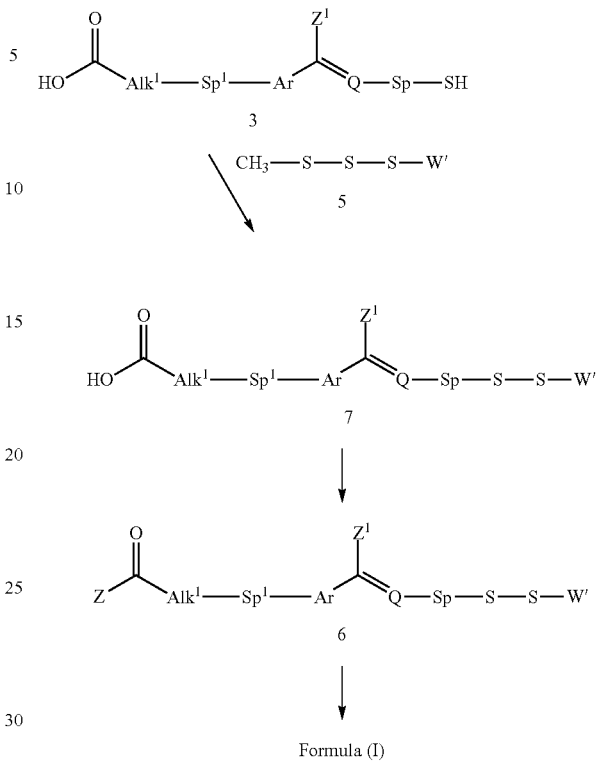

The following examples are presented to illustrate certain embodiments of the present invention, but should not be construed as limiting the scope of this invention. Those skilled in the art will readily understand that known variations of the conditions of the following preparative procedures can be used to prepare these compounds.

EXAMPLE 1

Butanoic acid, 3-mercapto-3-methyl-,2[(E)-1-[4-(4-hydroxy-4-oxobutoxy)phenyl]ethylidene]hydrazide

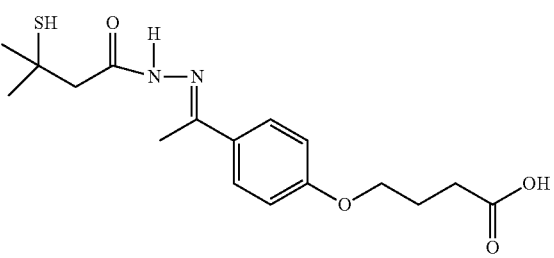 [SMILES: C/C(=N\NC(=O)CC(C)(C)S)c1ccc(OCCCC(=O)O)cc1]

To a stirred mixture of 0.5 g [3.4 mmol] of 3-methyl-3-mercapto-butanoic acid hydrazide in 5.0 ml of methanol is rapidly added 0.91 g [4.1 mmol] of 4-(4-acetylphenoxy)-butanoic acid followed by an additional 10 ml of methanol and 1.5 ml of acetic acid and stirring continued for 24 hours. The reaction mixture is filtered and the solid washed with 100 ml of methanol to give 0.78 g of the title compound as a solid.

EXAMPLE 2

Butanoic acid, 3-mercapto-3-methyl-,2-[(E)-1-[4-(4-hydroxy-4-oxobutoxy)phenyl]ethylidene]hydrazide

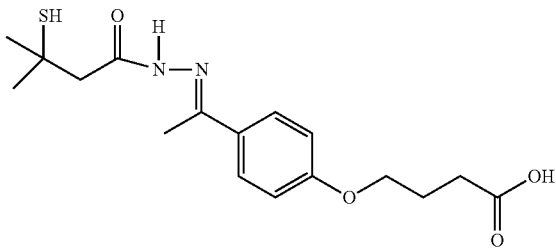 [SMILES: C/C(=N\NC(=O)CC(C)(C)S)c1ccc(OCCCC(=O)O)cc1]

A mixture of 3-methyl-3-mercapto-butanoic acid hydrazide (4.0 g, 27 mmol), 4-(4-acetylphenoxy)-butanoic acid (5.0 g, 22.5 mmol) and acetic acid (7.5 mL) in methyl alcohol (75 mL) is heated at about 45° C. for about 7 h. The mixture is allowed to cool to room temperature. The white solid (7.12 g, 90%) is collected on a Buchner funnel and washed with MeOH (2×10 mL). $^1$H NMR (DMSO-$d_6$): δ (ppm) 12.14 (s, 1H), 10.37 and 10.21 (s, 1H), 7.74-7.70 (m, 2H), 6.97-6.95 (m, 2H), 4.04 (t, 2H), 3.09 and 3.04 (s, 2H), 2.66 (s, 1H), 2.41-2.37 (t, 2H), 2.22 and 2.20 (s, 3H), 1.97-1.93 (m, 2H), 1.8 (s, 3H), 1.47 (s, 3H). MS: 375 ($M^+$+Na).

EXAMPLE 3

Butanoic acid, 3-mercapto-3-methyl-,2-[(E)-1-[4-[4-[(2,5-dioxo-1-pyrolidinyl)oxy]-4-oxobutoxy]phenyl]ethylidene]hydrazide

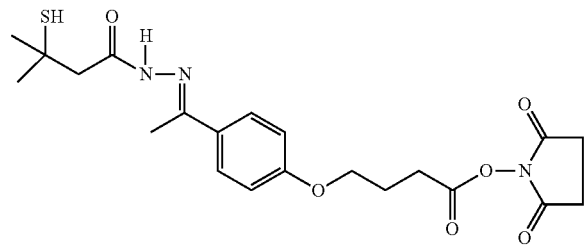 [SMILES: C/C(=N\NC(=O)CC(C)(C)S)c1ccc(OCCCC(=O)ON2C(=O)CCC2=O)cc1]

To a mixture of 0.5 g [1.42 mmol] of butanoic acid, 3-mercapto-3-methyl-,2-[(E)-1-[4-(4-hydroxy-4-oxobutoxy)phenyl]ethylidene]hydrazide (Example 1 or 2) and 0.22 g [1.89 mmol] of N-hydroxysuccinimide is added 10 ml of N,N-dimethylformamide followed by the rapid addition of 0.70 g [3.65 mmol] of 1-(3-dimethylaminopropyl)-3-ethylcarbodiimide hydrochloride and the mixture stirred at room temperature for 3 hours. The reaction mixture is concentrated in vacuo to a residue which is partitioned between ethyl acetate and water. The separated organic layer is washed with water, saturated sodium chloride and dried (MgSO$_4$). The organic layer is evaporated in vacuo to give an oily residue which crystallized from ethyl acetate-hexane affording 0.21 g of the title compound as a colorless solid.

EXAMPLE 4

Butanoic acid, 3-mercapto-3-methyl-,2-[(E)-1-[4-[4-[(2,5-dioxo-1-pyrrolidinyl)oxy]-4-oxobutoxyl]phenyl]ethylidene]hydrazide

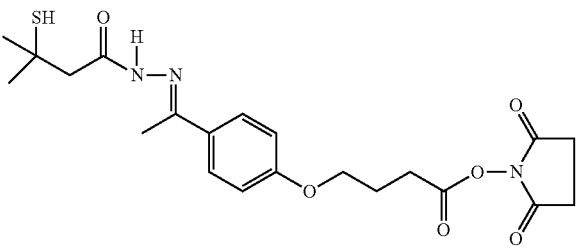 [SMILES: C/C(=N\NC(=O)CC(C)(C)S)c1ccc(OCCCC(=O)ON2C(=O)CCC2=O)cc1]

A mixture of butanoic acid, 3-mercapto-3-methyl-,2-[(E)-1-[4-(4-hydroxy-4-oxobutoxy)phenyl]ethylidene]hydrazide (Examples 1 or 2) (3.69 g, 10.48 mmol) and N-hydroxysuccinimide (1.386 g, 12.05 mmol) is suspended in dioxane (60 mL), DCC (2.482 g, 12.05 mmol) in dioxane (30 mL) is added dropwise over 15 min. The mixture is stirred at room temperature for 24 h. The precipitated dicyclohexylurea is filtered off and washed with dioxane (2×10 mL). The filtrate is concentrated to about 50 mL and while stirring, water (250 mL) is added. The resulting white solid is collected on a Buchner funnel, washed with water (2×50 mL), and dried in vacuo at room temperature. To this white solid is added MeCN (60 mL) and the mixture is heated at 50° C. until it became solution, isopropyl alcohol (IPA) (400 mL) is added. The mixture is then cooled to 0-5° C. for 2 h. The solid is collected on a Buchner funnel, washed with cold IPA (2×20 mL) an dried in vacuo to afford the product of the example as a white solid (3.58 g, 70%). MS: 450 ($M^+$+1).

EXAMPLE 5

Butanoic acid, 3-mercapto-3-methyl-,2-[(E)-1-[4-[4-[(2,5-dioxo-1-pyrrolidinyl)oxy]-4-oxobutoxy]phenyl]ethylidene]hydrazide condensed with N-acetyl-LL-E33288$\gamma_1^I$

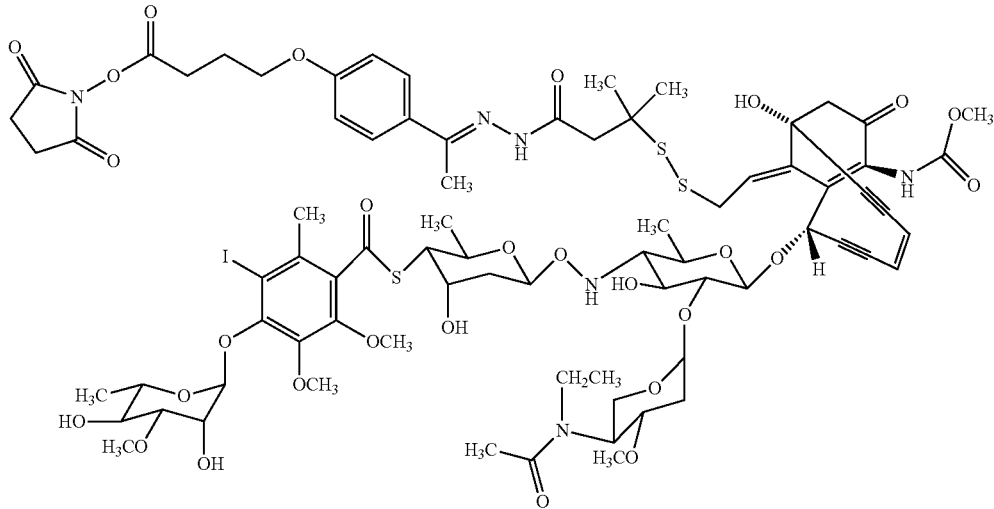

To a stirred solution of 0.505 g [1.12 mmol]butanoic acid, 3-mercapto-3-methyl-,2-[(E)-1-[4-[4-[(2,5-dioxo-1-pyrrolidinyl)oxy]-4-oxobutoxy]phenyl]ethylidene]hydrazide (Example 4) in 50 ml of acetonitrile is added 0.123 g [1.16 mmol] of sodium carbonate followed by heating at gentle reflux for 1 hour, cooled to room temperature and filtered. The filtrate is cooled to −15° C. and a solution of 1.4969 g [1.1 mmol] of N-acetyl-LL-E33288 $\gamma_1^I$ in 5 ml of acetonitrile added slowly by dropwise addition over 20 minutes and stirring continued for about 1.5 hours. The reaction mixture is allowed to warm to room temperature and stirred for about 3 hours. The volatiles are evaporated in vacuo to a residue which is stored in a freezer. To the residue is added 25 ml of ethyl acetate followed by storage in a freezer for about 1 hour. The reaction mixture is filtered and the ethyl acetate evaporated to a residue which is dissolved in 10 ml of ethyl acetate and applied to a column of 110 g of silica gel. The column is eluted with 1-5% methyl alcohol in ethyl acetate to give 0.322 g of the desired product having 65.27% purity as determined by HPLC.

EXAMPLE 6

Butanoic acid, 3-mercapto-3-methyl-,2-[(E)-1-[4-[4-[(2,5-dioxo-1-pyrrolidinyl)oxy]-4-oxobutoxy]phenyl]ethylidene]hydrazide condensed with N-acetyl-LL-E33288$\gamma_1^I$

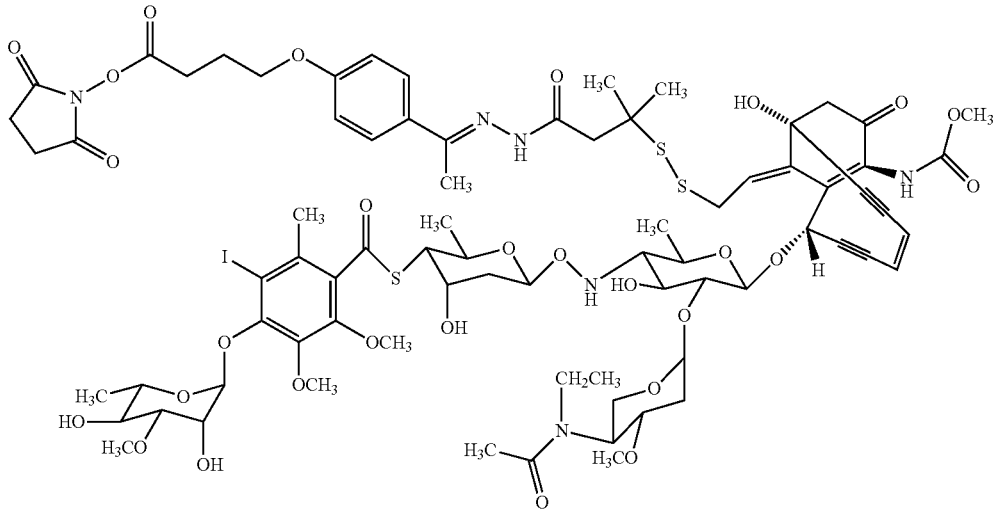

A solution of butanoic acid, 3-mercapto-3-methyl-,2-[(E)-1-[4-[4-[(2,5-dioxo-1-pyrrolidinyl)oxy]-4-oxobutoxy]phenyl]ethylidene]hydrazide (450 mg, 1 mmol) (Example 4) in CH$_3$CN (100 mL) containing Et$_3$N (0.35 mL) is treated with a solution of N-acetyl-LL-E33288 $\gamma_1^I$ (500 mg, 0.355 mmol) in CH$_3$CN (100 mL) at 0-5° C. The mixture is then stirred for another 1 h while cooling with a ice-bath. The solvent is removed and the residue is purified on a silica gel column eluting with CH$_2$Cl$_2$-MeOH to afford the product of the example (340 mg, 54%) as a white solid. MS: 1780 (M$^+$+1)

EXAMPLE 7

Butanoic acid, 3-mercapto-3-methyl-,2-[(E)-1-[4-(4-hydroxy-4-oxobutoxy)phenyl]ethylidene]hydrazide condensed with N-acetyl-LL-E33288$\gamma_1^I$

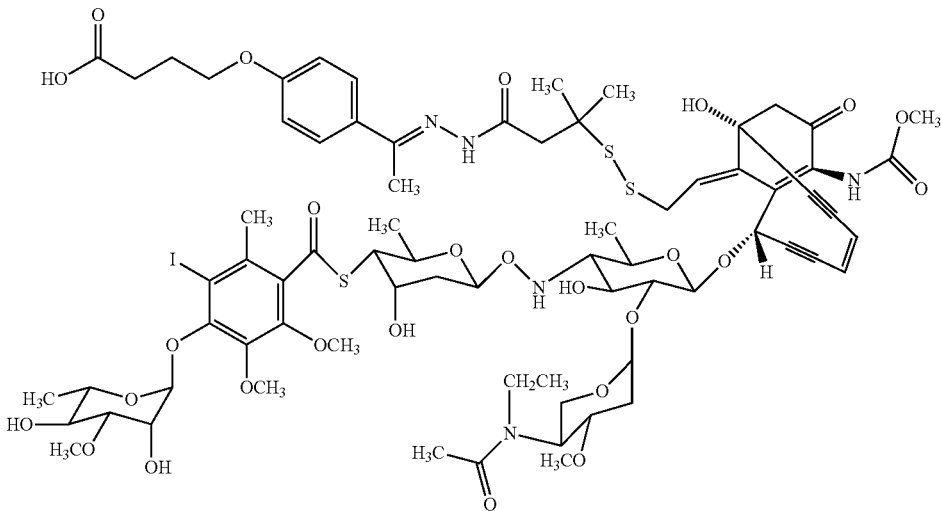

To a stirring solution of N-acetyl-LL-E33288 $\gamma_1^I$ (200 mg, 0.142 mmol) in 10 ml acetonitrile/ethyl acetate (1:1) at –5° C. is added in 1 ml aliquots every 10 min a solution of butanoic acid, 3-mercapto-3-methyl-,2-[(E)-1-[4-(4-hydroxy-4-oxobutoxy)phenyl]ethylidene]hydrazide (150 mg, 0.43 mmol) (Examples 1 or 2) in 10 ml acetonitrile/ethyl acetate (1:1) and 0.06 ml triethyl amine. The solution is stirred for two hours at –5° C. after the last addition of the butanoic acid, 3-mercapto-3-methyl-,2-[(E)-1-[4-(4-hydroxy-4-oxobutoxy)phenyl]ethylidene]hydrazide solution. The solvent was removed under reduced pressure and the residue is purified on a silica gel column eluting with CH$_2$Cl$_2$-MeOH to afford the product of the example as a white solid. MS 1684 (M$^+$+1)

EXAMPLE 8

Butanoic acid, 3-mercapto-3-methyl-,2-[(E)-1-[4-[4-[(2,5-dioxo-1-pyrrolidinyl)oxy]-4-oxobutoxy]phenyl]ethylidene]hydrazide condensed with N-acetyl-LL-E33288$\gamma_1^I$ To a stirring solution of butanoic acid, 3-mercapto-3-methyl-,2[(E)-1-[4-(4-hydroxy-4-oxobutoxy)phenyl]ethylidene]hydrazide with N-acetyl-LL-E33288$\gamma_1^I$ (100 mg, 0.059 mmol) in 0.5 mL of DMF and 1.8 mL of acetonitrile at 25° C. is added N-hydroxysuccinimide (236 mg, 2.05 mmol) and 1-(3-dimethylaminopropyl)-3-ethylcarbodiimide (160 mg 0.835 mmol). Following the addition, the solution is stirred for one hour at 25° C. The acetonitrile is removed under reduced pressure and the resulting DMF solution is added to 3 mL of stirring water giving a precipitate. The precipitate is filtered, dried and purified on a silica gel column eluting with CH$_2$Cl$_2$-isopropyl alcohol giving the product of the example (53 mg, 50%) obtained as a white solid. MS: 1780 (M$^+$+1)

What is claimed is:

1. A trifunctional linker intermediate, of the formula

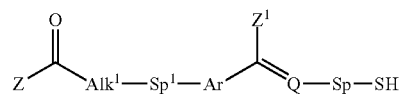

wherein:
Alk$^1$ is a branched or unbranched alkylene chain of 2 to 6 carbon atoms;
Sp$^1$ is selected from —S—, —O—, —CONH—, —NHCO—, and —NR'—;
Z$^1$ is H, or alkyl of 1 to 5 carbon atoms;
Ar is 1,2-, 1,3-, or 1,4-phenylene optionally substituted with one, two, or three groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR' or a 1,2-, 1,3-, 1,4-, 1,5-, 1,6-, 1,7-, 1,8-, 2,3-, 2,6-, or 2,7-naphthylidene optionally substituted with one, two, three, or four groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR';
n is an integer from 0 to 5;
R' is a straight or branched alkyl of 1 to 5 carbon atoms optionally substituted by one or two groups of —OH, alkoxy of 1 to 4 carbon atoms, thioalkoxy of 1 to 4 carbon atoms;
Sp is a straight or branched-chain divalent or trivalent alkyl radical of 1 to 18 carbon atoms, divalent or trivalent aryl or heteroaryl radical, divalent or trivalent cycloalkyl of 3 to 18 carbon atoms or heterocycloalkyl radical, divalent or trivalent aryl- or heteroaryl-alkyl (C1-C18) radical, divalent or trivalent cycloalkyl- or heterocyclo-alkyl-alkyl (C1-C18) radical or divalent or trivalent unsaturated alkyl radical of 2 to 18 carbon atoms, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by dialkylamino of 1 to 5 carbon atoms, alkoxy of 1 to 5 carbon atoms, hydroxy, or alkylthio of 1 to 5 carbon atoms groups;

Q is selected from the group consisting of —NNHCO—, —NNHCS—, and —NNHCONH—;

Z is selected from the group consisting of

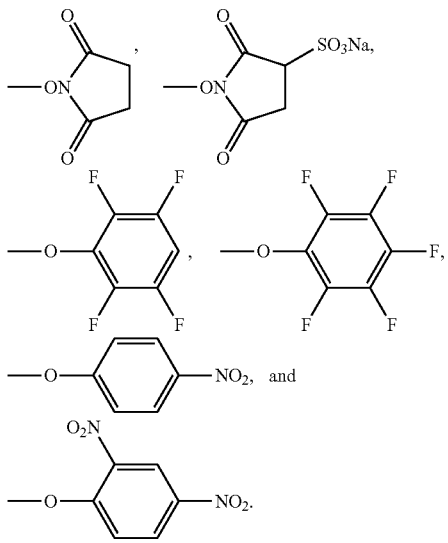

2. The trifunctional linker intermediate of claim 1, wherein Z is N-hydroxysuccinimide.

3. The trifunctional linker intermediate of claim 1, wherein Alk$^1$ is a branched or unbranched alkylene chain of 2 to 5 carbon atoms.

4. The trifunctional linker intermediate of claim 1, wherein Alk$^1$ is a branched or unbranched alkylene chain of 3 carbon atoms.

5. The trifunctional linker intermediate of claim 1, wherein Sp$^1$ is an oxygen atom.

6. The trifunctional linker intermediate of claim 1, wherein Z$^1$ is alkyl of 1 to 3 carbon atoms.

7. The trifunctional linker intermediate of claim 1, wherein Z$^1$ is methyl.

8. The trifunctional linker intermediate of claim 1, wherein Ar is selected from the group consisting of 1,2-phenylene, 1,3-phenylene, 1,4-phenylene, 1,2-naphthylidene, 1,3-naphthylidene, 1,4-naphthylidene, 1,5-naphthylidene, 1,6-naphthylidene, 1,7-naphthylidene, 1,8-naphthylidene, 2,3-naphthylidene, 2,6-naphthylidene, and 2,7-aphthylidene.

9. The trifunctional linker intermediate of claim 1, wherein Ar is 1,4-phenylene.

10. The trifunctional linker intermediate of claim 1, wherein Q is —NNHCO—.

11. The trifunctional linker intermediate of claim 1, wherein Sp is a straight or branched-chain divalent or trivalent alkyl radical of 1 to 12 carbon atoms.

12. The trifunctional linker intermediate of claim 1, wherein Sp is a straight or branched-chain divalent or trivalent alkyl radical of 1 to 6 carbon atoms.

13. The trifunctional linker intermediate of claim 1, wherein Sp is a straight or branched-chain divalent or trivalent alkyl radical of 4 carbon atoms.

14. The trifunctional linker intermediate of claim 1, having the formula:

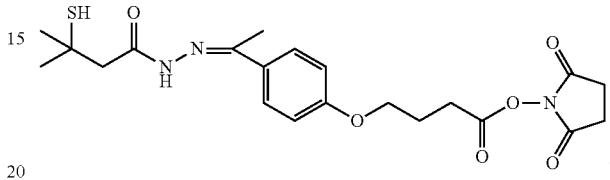

15. A sodium salt of the trifunctional linker intermediate of claim 1.

16. A bilinker carboxylic acid intermediate of the formula

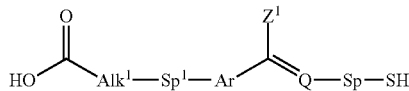

wherein:
Alk$^1$ is a branched or unbranched alkylene chain of 2 to 6 carbon atoms;
Sp$^1$ is selected from —S—, —O—, —CONH—, —NHCO—, and —NR'—;
Z$^1$ is H, or alkyl of 1 to 5 carbon atoms;
Ar is 1,2-, 1,3-, or 1,4-phenylene optionally substituted with one, two, or three groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR' or a 1,2-, 1,3-, 1,4-, 1,5-, 1,6-, 1,7-, 1,8-, 2,3-, 2,6-, or 2,7-naphthylidene optionally substituted with one, two, three, or four groups independently selected from alkyl of 1 to 6 carbon atoms, alkoxy of 1 to 5 carbon atoms, thioalkoxy of 1 to 4 carbon atoms, halogen, nitro, —COOR', —CONHR', —O(CH$_2$)$_n$COOR', —S(CH$_2$)$_n$COOR', —O(CH$_2$)$_n$CONHR', and —S(CH$_2$)$_n$CONHR';
n is an integer from 0 to 5;
R' is a straight or branched alkyl of 1 to 5 carbon atoms optionally substituted by one or two groups of —OH, alkoxy of 1 to 4 carbon atoms, thioalkoxy of 1 to 4 carbon atoms;
Sp is a straight or branched-chain divalent or trivalent alkyl radical of 1 to 18 carbon atoms, divalent or trivalent aryl or heteroaryl radical, divalent or trivalent cycloalkyl of 3 to 18 carbon atoms or heterocycloalkyl radical, divalent or trivalent aryl- or heteroaryl-alkyl (C$_1$-C$_{18}$) radical, divalent or trivalent cycloalkyl- or heterocyclo-alkyl-alkyl (C$_1$-C$_{18}$) radical or divalent or trivalent unsaturated alkyl radical of 2 to 18 carbon atoms, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by dialkylamino of 1 to 5 carbon atoms, alkoxy of 1 to 5 carbon atoms, hydroxy, or alkylthio of 1 to 5 carbon atoms groups; and Q is selected from the group consisting of —NNHCO—, —NNHCS—, and —NNHCONH—.

17. The bilinker carboxylic acid intermediate of claim 16, wherein $Alk^1$ is a branched or unbranched alkylene chain of 2 to 5 carbon atoms.

18. The bilinker carboxylic acid intermediate of claim 16, wherein $Alk^1$ is a branched or unbranched alkylene chain of 3 carbon atoms.

19. The bilinker carboxylic acid intermediate of claim 16, wherein $Sp^1$ is an oxygen atom.

20. The bilinker carboxylic acid intermediate of claim 16, wherein $Z^1$ is alkyl of 1 to 3 carbon atoms.

21. The bilinker carboxylic acid intermediate of claim 16, wherein $Z^1$ is methyl.

22. The bilinker carboxylic acid intermediate of claim 16, wherein Ar is selected from the group consisting of 1,2-phenylene, 1,3-phenylene, 1,4-phenylene, 1,2-naphthylidene, 1,3-naphthylidene, 1,4-naphthylidene, 1,5-naphthylidene, 1,6-naphthylidene, 1,7-naphthylidene, 1,8-naphthylidene, 2,3-naphthylidene, 2,6-naphthylidene, and 2,7-naphthylidene.

23. The bilinker carboxylic acid intermediate of claim 16, wherein Ar is 1,4-phenylene.

24. The bilinker carboxylic acid intermediate of claim 16, wherein Q is —NNHCO—.

25. The bilinker carboxylic acid intermediate of claim 16, wherein Sp is a straight or branched-chain divalent or trivalent alkyl radical of 1 to 12 carbon atoms.

26. The bilinker carboxylic acid intermediate of claim 16, wherein Sp is a straight or branched-chain divalent or trivalent alkyl radical of 1 to 6 carbon atoms.

27. The bilinker carboxylic acid intermediate of claim 16, wherein Sp is a straight or branched-chain divalent or trivalent alkyl radical of 4 carbon atoms.

28. The bilinker carboxylic acid intermediate of claim 16, having the formula:

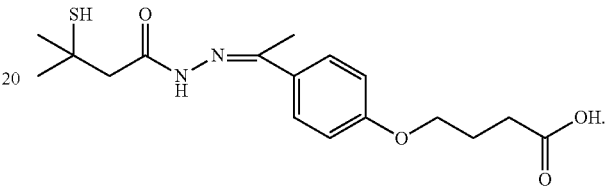

* * * * *